United States Patent [19]

Sugiyama

[11] 4,188,489

[45] Feb. 12, 1980

[54] PROCESS FOR THE PRODUCTION OF 3-SUBSTITUTED AMINO-5-PYRAZOLONES

[75] Inventor: Masatoshi Sugiyama, Minami-ashigara, Japan

[73] Assignee: Fuji Photo Film Co., Ltd., Minami-ashigara, Japan

[21] Appl. No.: 677,452

[22] Filed: Apr. 16, 1976

[30] Foreign Application Priority Data

Apr. 16, 1975 [JP] Japan ................................. 50-45996

[51] Int. Cl.$^2$ ........................................ C07D 231/52
[52] U.S. Cl. ............................. 548/360; 548/364; 548/365; 544/140; 544/371; 546/211; 260/239.9
[58] Field of Search ........... 260/310 A, 326.85, 293.7, 260/239.9; 548/365, 364, 360; 544/140, 371; 546/211

[56] References Cited

U.S. PATENT DOCUMENTS

| | | | |
|---|---|---|---|
| 3,152,896 | 10/1964 | Tuite | 260/310 A |
| 3,931,221 | 1/1976 | Meier et al. | 260/310 A |

FOREIGN PATENT DOCUMENTS 1449259 11/1966 France .
1007847 10/1963 United Kingdom ................. 260/310 A

OTHER PUBLICATIONS

Wiley et al., Heterocyclic Chemistry, Pyrazolones, Pyrazolidines and Derivative, p. 62.

*Primary Examiner*—Natalie Trousof
*Assistant Examiner*—Jane T. Fan
*Attorney, Agent, or Firm*—Sughrue, Rothwell, Mion, Zinn and Macpeak

[57] ABSTRACT

3-Substituted amino-5-pyrazolones containing at least one sulfo group represented by the formula:

$$R^2-(N-C)_l-N-C-CH_2$$

(with $R^1$, H, X, N, Q, C=O substituents shown)

and a process for producing the above pyrazolones by reacting a β-substituted amino-β-alkoxy acrylic acid derivative represented by the formula:

$$R^2+N-C)_l-N-C=CH-COY$$

(with $R^1$, H, X, $OR^3$ substituents shown)

and a hydrazine containing at least one sulfo group represented by the formula:

$$NH_2-NH-Q$$

wherein $R^1$ is a hydrogen atom, an aliphatic group, an aralkyl group or an aryl group; $R^2$ is an aliphatic group, an aralkyl group, a heterocyclic group, an aryl group or an acyl group; l is 0 or 1 and where l is 0, $R^1$ and $R^2$ may combine with each other to form an alkylene group or an alkylene group interrupted by a hetero atom; $R^3$ is an aliphatic group or an aralkyl group; X is oxygen or sulfur; Y is a hydroxy group, an alkoxy group, an aralkoxy group, or a primary, secondary or tertiary amino group; and Q is an aliphatic group, an aryl group, or an aralkyl group containing at least one sulfo group.

12 Claims, No Drawings

PROCESS FOR THE PRODUCTION OF 3-SUBSTITUTED AMINO-5-PYRAZOLONES

BACKGROUND OF THE INVENTION

1. Field of the Invention

The present invention relates to 3-substituted amino-5-pyrazolones and a process for producing the same. More particularly, the present invention is concerned with 3-substituted amino-5-pyrazolones containing at the 1-position a substituent containing at least one sulfo group and a process for producing the same.

2. Description of the Prior Art

The 3-substituted amino-5-pyrazolones containing a sulfo group or groups produced by the method of the present invention are important as magenta color formers (couplers) for silver halide color photographic light-sensitive materials, and, furthermore, as spectral sensitizers (for example, methine dyes) and dyes (for example, dyes for filters) for use in silver halide photographic light-sensitive elements.

The pyrazolones of the present invention are advantageous as compared to the corresponding 3-amino compounds in that since the absorption wavelength region thereof can be properly shifted into a longer wavelength region, color reproduction is improved, and, since the solubilities of the pyrazolones in the dye form in photographic processing solutions are high, contamination due to the dyes on a film or a photographic paper is low.

Although 3-amino-1-(4-sulfophenyl)-5-pyrazolones can be synthesized by reacting cyan acetic acid and p-sulfophenyl hydrazine by the method described in *Organic Synthesis*, Vol. 28, page 87 (1948), it is not possible to synthesize the corresponding 3-substituted amino compounds by this method. Several methods of producing 5-pyrazolones containing an anilino group as the substituted amino group at the 3-position are known. When these methods, however, disadvantages occur in that the processing steps are complicated, yields are low, or only pyrazolones with a specific structure can be used, and thus they are not applicable to the general production of 3-substituted amino-5-pyrazolones.

In the case of synthesizing pyrazolones containing a sulfo group or groups, the method of synthesizing 3-anilino-5-pyrazolones described in U.S. Pat. No. 2,343,703 cannot be used since, in accordance with this method, 3-amino-5-pyrazolone and aniline are condensed with the evolution of ammonia.

Also, the method of synthesizing 3-anilino-5-pyrazolones by the dehydration of pyrazolidine-3,5-dion and a substituted aniline as described in Japanese Patent Application (OPI) 92066/1974 cannot be used since the reaction does not proceed because of the low solubilities of reactants used.

British Pat. No. 1,007,847, in which a method of producing pyrazolones containing an acylamino, ureido or thioureido group as the substituent amino group is described, is directed to acylation, ureidation or thioureidation of 3-amino-5-pyrazolones and only discloses in detail the palmitoylation of 3-amino-5-pyrazolones containing a sulfo group in the potassium salt form. Thus, this method cannot be generally used as a method of synthesizing substituted amino-5-pyrazolones containing a sulfo group.

Organic compounds containing a sulfo group are often handled in the form of the alkali metal, alkaline earth metal or like salts throughout isolation or purification steps. Such alkali metal salts or alkaline earth metal salts are markedly water soluble, while their solubilities in organic solvents are markedly low. Thus they are suitable for use in reactions using aqueous systems, but not suitable for those using organic solvents. In effecting organic chemical reactions, an organic solvent system has advantages over an aqueous system in that various kinds of reactions can be carried out, and, furthermore, operations such as isolation, purification, etc., are easy.

Since the 3-substituted amino-5-pyrazolones containing a sulfo group can be handled in an organic solvent system, they can advantageously be subjected to various organic chemical reactions. There are various kinds of organic compounds containing a sulfo group which can be used as additives for photographic light-sensitive materials, and the production of these organic compounds can be carried out advantageously in an organic solvent system in the case that the sulfo group of the starting materials, i.e., the sulfo group-containing organic compound, e.g., a 3-substituted amino-5-pyrazolones, is in the form of a free acid or in the form of the ammonium or organic base (for instance, a primary, secondary or tertiary amine) salt thereof.

SUMMARY OF THE INVENTION

An object of the present invention is to provide 3-substituted amino-5-pyrazolones containing a sulfo group or groups and a process for producing the same.

Another object of the present invention is to provide 3-substituted amino-5-pyrazolones containing a sulfo group or groups, the sulfo group being obtained in the form of a free acid or the ammonium or organic base salt, and a process for producing the same.

These objects are attained as follows: 3-substituted amino-5-pyrazolones containing at least one sulfo group, preferably no more than 2 sulfo groups, represented by Formula I can be produced by reacting a β-substituted aminoacrylic acid derivative represented by Formula II and a hydrazine containing at least one sulfo group represented by Formula III in an organic acid-organic base system.

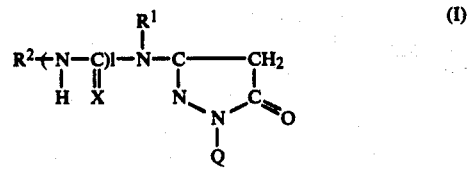

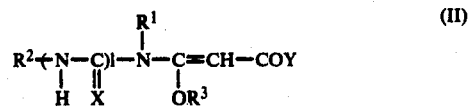

wherein $R^1$ is a hydrogen atom, an aliphatic group, an aralkyl group or an aryl group; $R^2$ is an aliphatic group (including, for example, a perfluorohydrocarbon group, an alkenyl group, an alicyclic hydrocarbon group), an aralkyl group, a heterocyclic group, an aryl group or an acyl group; l is 0 or 1 and where l is 0, $R^1$ and $R^2$ may combine with each other to form an alkylene group or an alkylene group interrupted by a hetero atom (for example, an oxygen atom or a nitrogen atom); $R^3$ is an aliphatic group or an aralkyl group; X is oxygen or sulfur; Y is a hydroxy group, an alkoxy group, an aralkoxy group or an amino group (including, for example, an alkylamino group, an aromatic amino group, an alicyclic amino group, a cyclic amino group containing a plurality of hetero atoms); and Q is an aliphatic group, an aryl group, or an aralkyl group containing at least one sulfo group.

DETAILED DESCRIPTION OF THE INVENTION

In formulae (I), (II), and (III), $R^1$ is preferably a hydrogen atom, a perfluoroalkyl group containing 1 to 12 carbon atoms, an alkyl group which is unsubstituted or, mono- or di-substituted, containing 1 to 18 carbon atoms (substituents usable herein include a halogen atom, an alkoxycarbonyl group (preferably $C_1$–$C_3$), an alkoxy group (preferably $C_1$–$C_4$), an aryloxy group (preferably $C_6$–$C_8$), etc.), a cycloalkyl group containing 5 to 7 carbon atoms, an aralkyl group containing 7 to 13 carbon atoms, or a monocyclic aryl group.

$R^2$ is preferably a perfluoroalkyl group containing 1 to 12 carbon atoms, an alkyl group which is unsubstituted or, mono- or di-substituted containing 1 to 18 carbon atoms (substituents usable herein include a halogen atom, an alkoxycarbonyl group (preferably $C_1$–$C_3$), an alkoxy group (preferably $C_1$–$C_4$), an aryloxy group (preferably $C_6$–$C_8$), etc.), an alkenyl group containing 2 to 5 carbon atoms, a cycloalkyl group containing 5 to 7 carbon atoms, an aralkyl group containing 7 to 13 carbon atoms, a 5- and/or 6-membered heterocyclic group containing 1 to 4 nitrogen atoms, or oxygen, sulfur or selenium atoms, a monocyclic or dicyclic aryl group, or a carboxylic acyl group, a sulfo acyl group or a phospho acyl group.

$l$ is 0 or 1, and where $l$ is 0, $R^1$ and $R^2$ may combine with each other to form an alkylene group containing 4 to 5 carbon atoms, or an alkylene group interrupted with a hetero atom, e.g., an oxygen atom or a nitrogen atom, containing 3 to 4 carbon atoms.

$R^3$ is an aliphatic group containing 1 to 6 carbon atoms e.g., methyl, ethyl, propyl, n-butyl, etc., or an aralkyl group containing 7 to 8 carbon atoms.

X is an oxygen atom or a sulfur atom.

Y is preferably a hydroxy group, an alkoxy group containing 1 to 6 carbon atoms, an alkoxy group containing 7 to 13 carbon atoms, an unsubstituted amino group, an alkylamino group containing 1 to 6 carbon atoms, an alicyclic amino group containing 1 to 6 carbon atoms, a cyclic amino group containing a one or more hetero atoms (for example, nitrogen or oxygen) in the ring, for example, a nitrogen atom which forms a 5- or 6-membered heterocyclic together with carbon atoms or with carbon atoms and a hetero atom (e.g., nitrogen or oxygen), e.g., a 5- or 6-membered cyclic amine group such as

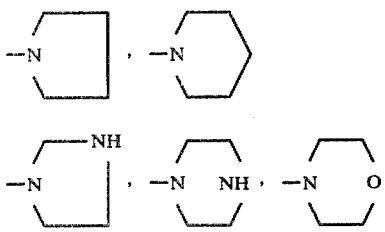

(each corner represents "$CH_2$") or an aromatic amino group, preferably a $C_6$–$C_8$ aromatic amine (for example,

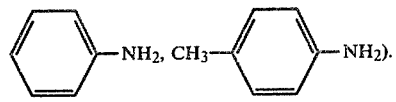

Q is preferably an aliphatic group containing at least one sulfo group, preferably no more than two sulfo groups, such as alkyl containing 1 to 6 carbon atoms, substituted alkyl containing 2 to 5 carbon atoms and one substituent thereof is a sulfo group and another substituent is hydroxy, alkoxy (preferably, $C_1$–$C_3$), halogen and alkenyl (preferably, $C_2$–$C_5$) whose total carbon atom number exclusive of those in the substituents is not more than 5; an aryl group containing at least one sulfo group, such as monocyclic or dicyclic aryl, a substituted aryl group substituted with a substituent or substituents other than the sulfo group, e.g., halogen, hydroxy, aryloxy (preferably, $C_6$–$C_8$), alkyl (preferably, $C_1$–$C_3$), sulfonyl, amino, and the like, wherein the sulfo group may be substituted onto the aryl group through an alkylene group, e.g.,

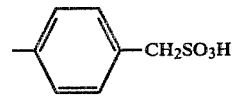

or an aralkyl group containing at least one sulfo group, e.g.,

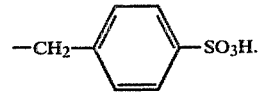

As more preferred embodiments of the present invention, the following are given.

$R^1$ is hydrogen, a perfluoroalkyl group containing 1 to 6 carbon atoms, e.g., n-perfluorobutyl, an alkyl group containing 1 to 6 carbon atoms, e.g., methyl, ethyl, n-propyl, i-propyl, n-butyl, i-butyl, n-pentyl, n-hexyl, and the like, a cycloalkyl group containing 5 to 6 carbon atoms, e.g., cyclopentyl, cyclohexyl, and the like, an aralkyl group containing 7 to 10 carbon atoms, e.g., benzyl, phenethyl, and the like, and a monocyclic aryl group, e.g., phenyl, tolyl, 4-chlorophenyl, 4-nitrophenyl, 4-methoxyphenyl, and the like.

$R^2$ is a perfluoroalkyl group containing 1 to 6 carbon atoms, e.g., n-perfluorobutyl, alkyl containing 1 to 6 carbon atoms, e.g., methyl, ethyl, n-propyl, i-propyl, n-butyl, i-butyl, n-pentyl, n-hexyl, and the like, a monosubstituted alkyl group containing 1 to 8 carbon atoms, e.g., chloromethyl, β-chloroethyl, γ-chloropropyl, ethoxycarboxymethyl, β-ethoxyethyl, α-ethoxyethyl, α-butoxyethyl, α-phenoxyethyl, 2-chloro-2-methylpropyl, 2-methyl-2-chloromethylpropyl, and the like, an alkenyl group containing 2 to 4 carbon atoms, e.g., vinyl, allyl, isopropenyl, methallyl, and the like, a cycloalkyl group containing 5 to 6 carbon atoms, e.g., cyclopentyl, cyclohexyl, and the like, an aralkyl groups containing 7 to 10 carbon atoms, e.g., benzyl, phenethyl, and the like, a heterocyclic ring, preferably a 5- and/or 6-membered ring, e.g., 2-thienyl, and a monocyclic aryl group, e.g., phenyl, a substituted phenyl group (substituents, for example, are alkyl (preferably, $C_1$-$C_3$), alkoxy (preferably $C_1$-$C_3$), acylamino (preferably $C_2$-$C_5$), alkoxy carbonyl (preferably $C_1$-$C_3$), halogen, nitro, sulfo, and the like), acyl, particularly (i) alkylsulfonyl containing 1 to 4 carbon atoms (for example, methanesulfonyl, ethanesulfonyl, propanesulfonyl, and the like), (ii) arylsulfonyl, preferably containing 6 to 8 carbon atoms (for example, benzenesulfonyl, tolyl, and the like), and (iii) carboxylic acyl, containing 2 to 8 carbon atoms in which the OH of the carboxy group is removed (for example, acetyl, propionyl, benzoyl, and the like).

Where l is 0, $R^1$ and $R^2$ may combine with each other to form an alkylene chain containing 4 to 5 carbon atoms (for example, a linkage forming a pyrrole or a piperidine ring) or an alkylene chain interrupted with a hetero atom such as nitrogen, oxygen or sulfur (for example, morpholine, piperazine, the only limitation being that the hetero atom is between the two terminal carbons of the alkylene group.

$R^3$ is an alkyl group containing 1 to 4 carbon atoms, e.g., methyl, ethyl, propyl, butyl, and the like, a monosubstituted alkyl group whose alkyl radicals contain 2 to 4 carbon atoms (substituents include halogen, e.g., chlorine and the like, alkoxy (preferably $C_1$-$C_4$), e.g., methoxy, ethoxy, propoxy, and the like), or aralkyl (preferably $C_7$-$C_9$), e.g., benzyl, phenethyl, and the like.

Y is hydroxy, an alkoxy group containing 1 to 4 carbon atoms, e.g., methoxy, ethoxy, n-propoxy, i-propoxy, n-butoxy, i-butoxy, and the like, an aralkoxy group containing 7 to 8 carbon atoms, e.g., benzyloxy, phenethoxy, and the like, an amino group, an alkylamino group containing 1 to 4 carbon atoms in any alkyl moiety present, e.g., methylamino, ethylamino, n-propylamino, n-butylamino, dimethylamino, diethylamino, and the like, an amino group which forms a heterocyclic ring containing 4 to 6 carbon atoms, e.g., pyrrolidine, piperidine, and the like, or an amino group which forms a saturated or unsaturated heterocyclic ring containing one or two hetero atoms in the ring, preferably two, (e.g., pyrazoline, piperazine, morpholine, and the like).

Q is an alkyl group containing at least one sulfo group and containing 1 to 5 carbon atoms, e.g., 2-sulfoethyl, 3-sulfopropyl, 2-sulfo-2-methylethyl, 4-sulfobutyl, 3-sulfo-3-methylpropyl, 4-sulfo-1-methylbutyl, and the like, an alkenyl group containing 2 to 4 carbon atoms, e.g., 3-sulfo-2-propenyl, a substituted alkyl group containing 3 to 6 carbon atom having substituents such as sulfo, hydroxy, alkoxy and the like, e.g., 4-sulfo-2-hydroxybutyl, 1-sulfo-2-hydroxypropyl, 4-sulfo-2-methoxybutyl, and the like, or an aryl group, preferably a mono- or di-cyclic aryl group, substituted with at least one sulfo group or a sulfoalkyl group (preferably, $C_1$-$C_4$), e.g., 4-sulfophenyl, 3-(sulfomethyl)-phenyl, 4-(δ-sulfobutyl)-phenyl, 2,5-disulfophenyl, 2,4-disulfophenyl, 3,5-disulfo-phenyl, 2-chloro-4-sulfophenyl, 4-phenoxy-3-sulfophenyl, 4,8-disulfonaphthyl-(2), 6,8-disulfonaphthyl-(2), 5-oxy-7-sulfonaphthyl-(2), and the like.

Preferred classes of materials also include the following:

When, l=0, $R^1$ is hydrogen, an aliphatic group, an aralkyl group, an aryl group or $R^1$ and $R^2$ are combined with each other to form an alkylene group or an alkylene group interrupted by a hetero atom, and $R^2$ is an aliphatic group, an aralkyl group, an aryl group, or an acyl group, where $R_3$ and Y are as defined above, and when l=1, $R^1$ is hydrogen, $R^2$ is an aliphatic group, an aralkyl group, an aryl group, a heterocyclic group, or an acyl group, where $R_3$ is as defined above, X is O or S and Y is as defined above.

The sulfo group in the form of the free acid or the ammonium or organic base salt thereof is particularly advantageous from the viewpoint of ease of synthesis. In particular, the form of the free acid or the organic base salt is preferred.

The sulfo groups of the sulfo group-containing 3-substituted amino-5-pyrazolones produced by the method of the present invention, which are in the form of the free acid or the ammonia or organic base salt, may be converted in the form of the alkali metal or alkaline earth metal salts thereof, if desired. For instance, the potassium salt can be deposited and isolated by adding a solution of potassium acetate or potassium hydroxide in methanol to a pyrazolone solution.

Preferred formation condition are as follows: Pressure: atmospheric; Temperature: 0° to 100° C., more preferably 10° to 60° C.; Amount of potassium acetate or potassium hydroxide added: from equimolar to twice the moles of the 3-substituted amino-5-pyrazolone(s); Time: from 30 minutes to 1 hour after dropping of the solution of potassium acetate or potassium hydroxide in methanol; Concentration of the methanol solution of potassium acetate or potassium hydroxide added; 5 to 50 wt%.

In a solution of the alkali metal or alkaline earth metal salt of the pyrazolone, however, it is quite difficult to convert the sulfo group in the form of a free acid or the amine salt thereof and then isolate, i.e., the conversion of $SO_3Na$ to $SO_3H.NR_3$ is quite difficult since $SO_3H$ is a strong acid and $SO_3Na$ is a salt of strong acid-strong base. However, $SO_3H$ or $SO_3H.NR_3$ is easily produced by the process of this invention.

One of the important features of the present invention resides in that the reaction between the acrylic acid derivative of Formula (II) and the sulfo group-containing hydrazine of Formula (III) is carried out in a mixture of an organic acid and an organic base.

General conditions for the reaction are often: Pressure: atmospheric;

Temperature: 0° to 150° C., more preferably 0° to 100° C., most preferably 10° to 50° C.;

Time of reaction: 2 hrs to 7 days; Ratio of Compound (II): Compound (III) 5:1, more preferably 3:1, most preferably 1.5:1 (molar);

Ratio of Compound (II): organic acid=1:(0.5–50 molar).

The preferred organic acids are aliphatic acids containing 1 to 5 carbon atoms. The organic base can be any primary, secondary or tertiary aliphatic or aromatic amine, and preferred organic bases are piperidine, morpholine, picoline, pyridine, aniline, o-toluidine, triethylamine, diethylamine, diisopropylamine, n-dibutylamine, n-tributylamine, diisobutylamine, quinoline, and the like.

Even more preferred organic acids are formic acid, acetic acid, and propionic acid, and even more preferred organic bases are triethylamine, n-tributylamine, diisopropylamine, piperidine, and diethylamine. In particular, it is most preferred that acetic acid and triethylamine be used in combination with each other.

The organic base is added in such an amount that the molar ratio thereof to the sulfo group-containing hydrazine (III) used in the present invention is about 0.5 to about 50, and the organic acid is added in such an amount that the molar ratio thereof to the organic base is about 0.1 to about 20. The molar ratio of the organic base to the hydrazine is preferably 0.5 to 20, more preferably 0.5 to 10, and the molar ratio of the organic acid to the organic base is preferably 0.5 to 10, more preferably 0.5 to 5.

To mixtures of organic acids and organic bases in which acrylic acid derivatives of Formula (II) and sulfo group-containing hydrazines are reacted, there can be added organic solvents such as alcohols, nitriles, amides, ketones, and the like.

Preferred alcohols include alcohols containing 1 to 5 carbon atoms, such as methanol, ethanol, n-propyl alcohol, i-propyl alcohol, n-butyl alcohol, n-pentyl alcohol, and the like. Preferred nitriles include acetonitrile, propionitrile, malonitrile, and the like. Preferred amides include dimethylformamide, dimethylacetoamide, dimethylpropioamide, and the like. Preferred ketones include acetone, methyl ethyl ketone, and the like.

As more preferred alcohols, nitriles, amides, and ketones there are used, respectively, methanol, ethanol and i-propyl alcohol; acetonitrile; dimethylformformamide and dimethylacetoamide; and acetone.

The method of the present invention is usually effected at temperatures of from about 0° C. to the boiling point of the mixture of an organic acid and an organic base, or a mixture of the organic acid, organic base and solvent.

The reaction time is determined relatively to the above reaction temperature, and it ranges from about 2 hours to about 7 days.

The end point of the reaction can be determined by various methods. For instance, a portion of the reaction mixture is reacted with a color developing agent (for example, a primary amino developing agent such as 4-amino-N,N-dialkylaniline, e.g., 4-amino-3-methyl-N,N-diethylaniline and the like) and then the degree of magenta color development is observed. Alternatively, a portion of the reaction mixture can be subjected to thin layer chromatography and its spectrum observed to confirm the degree of 5-pyrazolones produced.

The acrylic acid derivatives represented by Formula (II) can be synthesized either by the reaction of a β,β-alkoxyacrylic acid ester and amides as described in British Pat. Nos. 1,129,333 and 1,129,334 or by the reaction of a β-amino-β-alkoxyacrylic acid ester and any of an acid halide, sulfonyl chloride, isocyanate or thioisocyanate.

Preferred conditions for this reaction are:
Pressure: atmospheric;
Temperature: 0° to 120° C., more preferably 10°–80° C.;
Time: 2 hrs to 7 days;
Solvent: solvent as described above for the reaction of Compounds of Formulae (II) and (III).

Representative examples of the acrylic acid derivatives are shown below:
Ethyl β-amino-β-methoxyacrylate
Ethyl β-amino-β-ethoxyacrylate
Butyl β-amino-β-butoxyacrylate
Ethyl β-amino-β-phenoxyacrylate
Benzyl β-amino-β-benzyloxyacrylate
β-Amino-β-ethoxyacrylamide
β-Amino-β-ethoxyacrylic acid
Isopropyl β-amino-β-isopropoxyacrylate
Ethyl β-amino-β-(β'-chloroethoxy)acrylate
Ethyl β-amino-β-(β'-sulfoethoxy)acrylate Typical examples of useful acid halides are acetyl chloride, acetyl bromide, propionyl chloride, n-butyryl chloride, n-valeryl chloride, octanoyl chloride, furoyl chloride, α-thienoyl chloride, nicotinyl chloride, benzoyl chloride, phenylacetyl chloride, p-methylbenzoyl chloride, p-isopropylbenzoyl chloride, acrylic chloride, chloroacetyl chloride, trifluoroacetyl chloride, β-chloropropionyl chloride, α-bromocyclohexanecarbonyl bromide, o-chlorobenzoyl chloride, p-chlorobenzoyl chloride, methoxyacetyl chloride, β-methoxypropionyl chloride, β-ethoxypropionyl chloride, p-methoxybenzoyl chloride, cyanoacetyl chloride, p-nitrobenzoyl chloride, m-chlorosulfonylbenzoyl chloride, and the like.

Representative examples of useful sulfonyl chlorides are methanesulfonyl chloride, ethanesulfonyl chloride, 3-chloropropanesulfonyl chloride, benzenesulfonyl chloride, p-chlorobenzenesulfonyl chloride, p-nitrobenzenesulfonyl chloride, 1-heptanesulfonyl chloride, m-carboxybenzenesulfonyl chloride, p-toluenesulfonyl chloride, and the like.

Representative examples of useful thioisocyanates and isocyanates are methyl isocyanate, ethyl isocyanate, n-propyl isocyanate, i-propyl isocyanate, n-butyl isocyanate, i-butyl isocyanate, n-pentyl isocyanate, n-hexyl isocyanate, n-undecyl isocyanate, chloromethyl isocyanate, β-chloroethyl isocyanate, γ-chloropropyl isocyanate, ethoxycarbonylmethyl isocyanate, β-ethoxyethyl isocyanate, α-ethoxyethyl isocyanate, α-butoxyethyl isocyanate, α-phenoxyethyl isocyanate, 2-chloro-2-methylpropyl isocyanate, 2-methyl-2-chloromethyl isocyanate, cyclopentyl isocyanate, cyclohexyl isocyanate, benzyl isocyanate, phenethyl isocyanate, diphenylmethyl isocyanate, phenyl isocyanate, p-tolyl isocyanate, 4-biphenyl isocyanate, p-nitrophenyl isocyanate, p-methoxyphenyl isocyanate, p-ethoxyphenyl isocyanate, p-ethoxycarbonyl isocyanate, p-dimethylaminophenyl isocyanate, vinyl isocyanate, ally isocyanate, methanesulfonyl isocyanate, ethanesulfonyl isocyanate, benzenesulfonyl isocyanate, p-toluenesulfonyl isocyanate, acetyl isocyanate, propionyl isocyanate, benzoyl isocyanate, methyl isothiocyanate, ethyl isothiocyanate, allyl isothiocyanate, methallyl isothiocyanate, phenyl isothiocyanate, p-chlorophenyl isothiocyanate, benzoyl isothiocyanate, 2-thienyl isocyanate, 4,4'-methylene diphenyl isocyanate, and the like.

Examples of the methods of synthesizing the acrylic acid derivatives represented by Formula (II) by reacting a β-amino-β-alkoxyacrylic acid ester with any of an acid halide, sulfonyl chloride, isocyanate or thioisocyanate are shown below. Unless otherwise indicated, processing was at atmospheric pressure.

PREPARATION EXAMPLE 1

Synthesis of Ethyl-β-benzoylamino-β-ethoxy Acrylate

To a solution of 15.9 g of ethyl-β-amino-β-ethoxy acrylate in 70 ml of benzene was added 10.2 g of triethylamine, and a solution of 14 g of benzoyl chloride in 30 ml of benzene was slowly dropped thereinto over period of 30 minutes while cooling with water and stirring. After the dropping, the resulting mixture was boiled on a steam bath for 6 hours. The crystals deposited were separated, and the filtrate washed with water and dried over anhydrous sodium sulfate. The benzene was then distilled away and the residue distilled under reduced pressure. 17 g of ethyl-β-benzoylamino-β-ethoxyacrylate of a boiling point of 136°–137° C./1 mmHg was obtained.

PREPARATION EXAMPLE 2

Synthesis of Ethyl-β-methanesulfonylamino-β-ethoxy Acrylate

To a solution of 15.9 g of ethyl-β-amino-β-ethoxy acrylate in 60 ml of benzene was added 10.3 g of triethylamine, and a solution of 11.5 g of methanesulfonyl chloride in 40 ml of benzene was dropped thereinto with stirring. After the dropping, the resulting mixture was stirred at room temperature for 5 hours. The crystals formed were separated. The filtrate was concentrated under reduced pressure and the concentrated residue crystallized by cooling. When the crystals were washed with n-hexane and dried, 16 g of prismatic crystals of a melting point of 103° to 104° C. was obtained.

PREPARATION EXAMPLE 3

Synthesis of Ethyl-β-methylureido-β-ethoxy Acrylate

To a solution of 15.9 g of ethyl-β-amino-β-ethoxy acrylate in 30 ml of acetonitrile was added 5.7 g of methyl isocyanate, and the resulting mixture was allowed to stand at room temperature for one day and one night. The acetonitrile was distilled away in vacuum, and to the residue obtained there was added 100 ml of ether, the system then being dried over anhydrous sodium sulfate. The ether was distilled away and the residue obtained was distilled under reduced pressure. 12 g of ethyl-β-methylureido-β-ethoxyacrylate of a boiling point of 129° to 132° C./1 mmHg was thus obtained.

PREPARATION EXAMPLE 4

Synthesis of Ethyl-β-ethylureido-β-ethoxy Acrylate

To a solution of 15.9 g of ethyl-β-amino-β-ethoxy acrylate in 30 ml of acetonitrile was added 7.1 g of ethyl isocyanate, and the resulting mixture was allowed to stand at room temperature for one day and one night. The acetonitrile was distilled away under reduced pressure. To the residue was added 100 ml of ether and the system then dried over anhydrous sodium sulfate. The ether was distilled away and the residue was distilled under reduced pressure. Thus, 14 g of ethyl-β-ethylureido-β-ethoxy acrylate of a boiling point of 127° to 130° C. was obtained.

PREPARATION EXAMPLE 5

Synthesis of Ethyl-β-phenylureido-β-ethoxy Acrylate

Into a solution of 15.9 g of ethyl-β-amino-β-ethoxy acrylate in 30 ml of acetonitrile there was dropped 11.9 g of phenyl isocyanate while cooling, and the resulting mixture was allowed to stand at room temperature for 5 hours. The acetonitrile was then distilled away. To the residue was added 100 ml of ether, which was then dried over anhydrous sodium sulfate. The ether was distilled away and the residue obtained was distilled under reduced pressure. Thus, 12 g of ethyl-β-phenylureido-β-ethoxy acrylate of a boiling point of 83° to 84° C./0.5 mmHg was obtained.

PREPARATION EXAMPLE 6

Synthesis of β-N-Piperidino-β-ethoxy Acrylic Piperidide

Twenty one grams of ethyl-β,β-diethoxyacrylate and 17 g of piperidine were heated at 130° C. for 10 hours, and the reaction solution concentrated under reduced pressure. To the concentrated residue was added benzene and the system then dried over anhydrous sodium sulfate. The benzene was distilled away under reduced pressure, and the residue was distilled under reduced pressure. Thus, 26 g of β-N-piperidino-β-ethoxy acrylic piperidide of a boiling point of 152° to 155° C./2 mmHg (melting point of 38° to 40° C.) was obtained.

PREPARATION EXAMPLE 7

Synthesis of β-N-Morpholino-β-ethoxyacrylic Morpholide

Twenty seven grams of ethyl-β,β-diethoxy acrylate and 19 g of morpholine were boiled on a steam bath for 5 hours. The reaction mixture was then concentrated under reduced pressure. To the concentrated residue was added 30 ml of isopropyl alcohol, and, upon standing for one night, crystals deposited. These crystals were recrystallized from ethanol and thus 31 g of crystals of the objective compound which had a melting point of 139° to 141° C. was obtained.

Examples of the compounds represented by Formula (II) are shown below:
Ethyl-β-(N,N-di-n-butyl)amino-β-ethoxyacrylate
Ethyl-β-(N-methyl-N-octadecyl)amino-β-ethoxyacrylate
Ethyl-β-(N,N-dibenzyl)amino-β-ethoxyacrylate
Ethyl-β-(N,N-di-n-hexyl)amino-β-ethoxyacrylate
Ethyl-β-acetylamino-β-ethoxyacrylate
Ethyl-β-benzoylamino-β-ethoxyacrylate
Ethyl-β-methanesulfonylamino-β-ethoxyacrylate
Ethyl-β-(p-toluenesulfonyl)amino-β-ethoxyacrylate
Ethyl-β-anilino-β-ethoxyacrylate
Ethyl-β-(3,5-dimethoxycarbonyl)anilino-β-ethoxy acrylate
Ethyl-β-(4-nitro)anilino-β-ethoxyacrylate
Ethyl-β-(2-thienyl)uredio-β-ethoxyacrylate
Ethyl-β-methylureido-β-ethoxyacrylate
Ethyl-β-ethylureido-β-ethoxyacrylate
Ethyl-β-n-butylureido-β-ethoxyacrylate
Ethyl-β-phenylureido-β-ethoxyacrylate
Ethyl-β-(2-chloroethyl)ureido-β-ethoxyacrylate
Ethyl-β-acetylureido-β-ethoxyacrylate
Ethyl-β-benzoylureido-β-ethoxyacrylate
Ethyl-β-methanesulfonylureido-β-ethoxyacrylate
Ethyl-β-n-butylamino-β-ethoxyacrylate
Ethyl-β-phenylthioureido-β-ethoxyacrylate
β-morpholino-β-ethoxyacrylic morpholide
β-piperidino-β-ethoxyacrylic piperidide
β-pyrolidino-β-ethoxyacrylic pyrolidide
β-(4-methylpiperidino)-β-ethoxyacrylic (4-methylpiperidide)

Representative examples of the compounds represented by Formula (III) are shown below:

$$NH_2NHCH_2CH_2SO_3H$$
$$NH_2NHCH_2CH_2CH_2SO_3H$$
$$NH_2NHCH_2CH_2CH_2CH_2SO_3H$$
$$NH_2NHCHCH_2CH_2CH_2CH_2SO_3H$$
$$| \atop CH_3$$
$$NH_2NHCH_2CHCH_2SO_3H$$
$$| \atop OH$$
$$NH_2NHCH_2CH=CHSO_3H$$
$$NH_2NHCH_2CH_2CH_2CH_2CH_2SO_3H$$

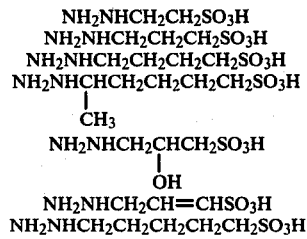
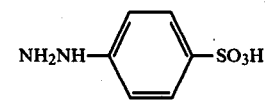

-continued
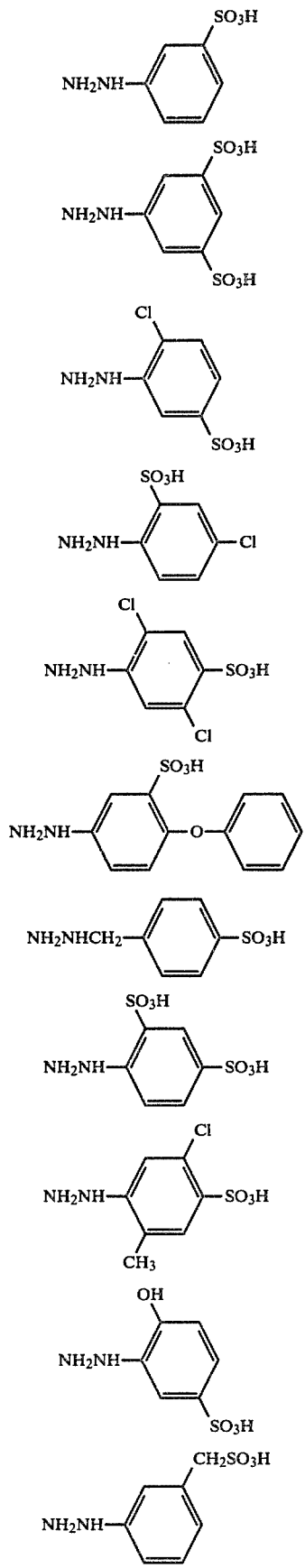
-continued
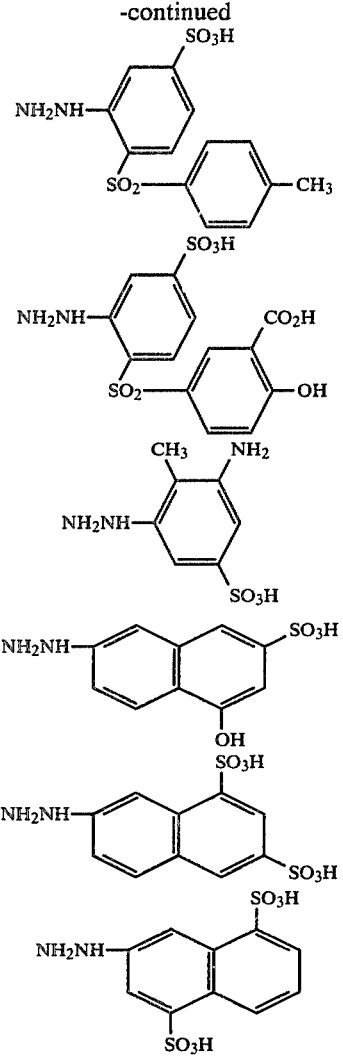
Representative examples of the compounds represented by Formula (I) are shown below:
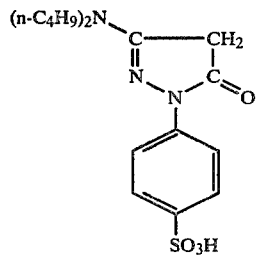
Compound 1
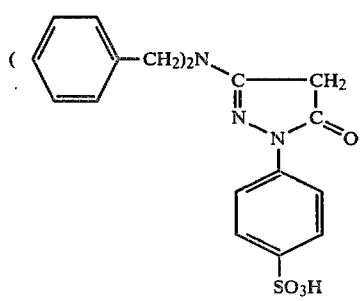
Compound 2

-continued
Compound 3
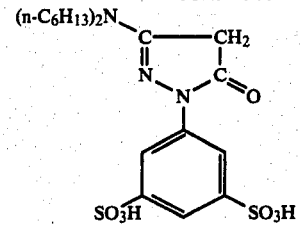
Compound 4
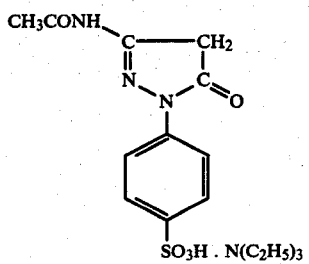
Compound 5
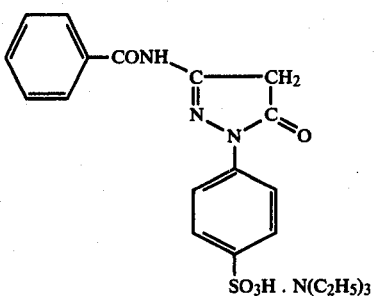
Compound 6
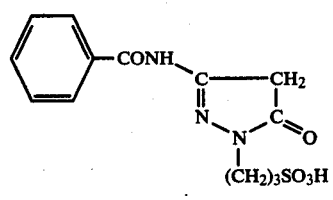
Compound 7
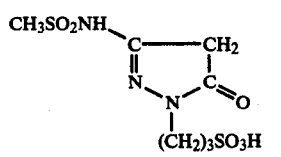
Compound 8
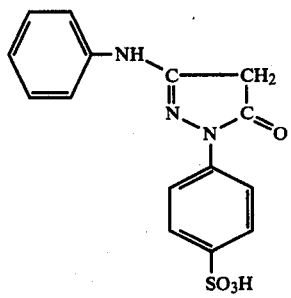
Compound 9
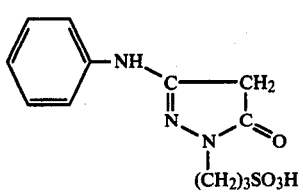
-continued
Compound 10
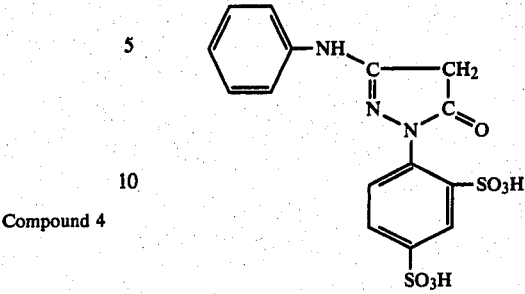
Compound 11
Compound 12
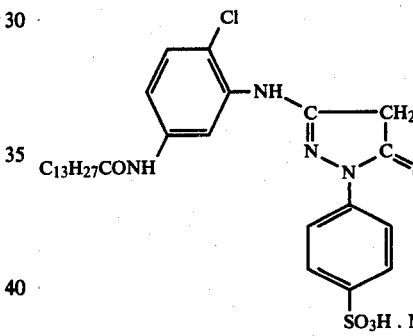
Compound 13
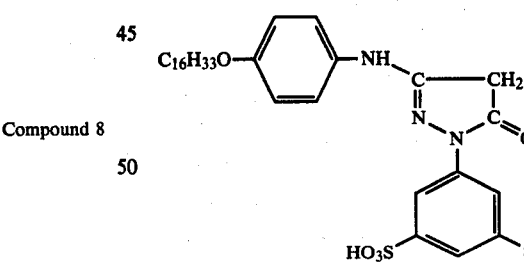
Compound 14
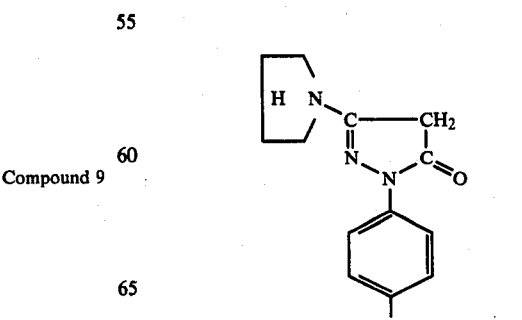
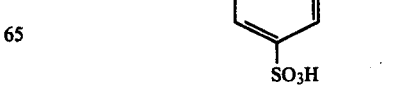

-continued
Compound 15
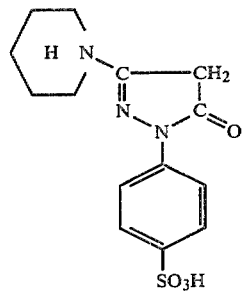
Compound 16
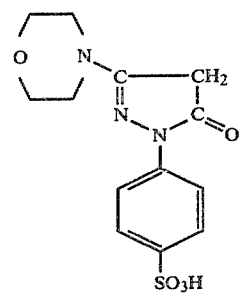
Compound 17
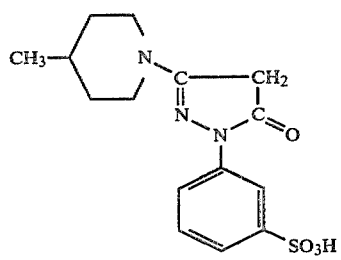
Compound 18
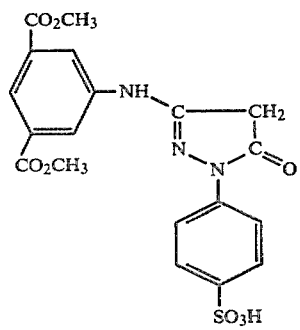
Compound 19
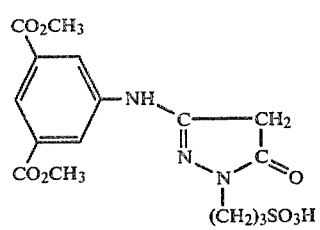
-continued
Compound 20
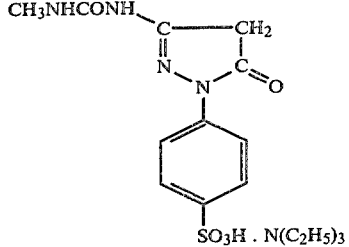
Compound 21
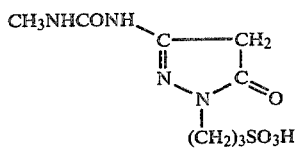
Compound 22
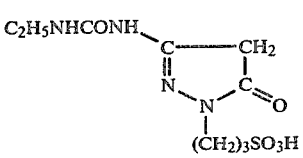
Compound 23
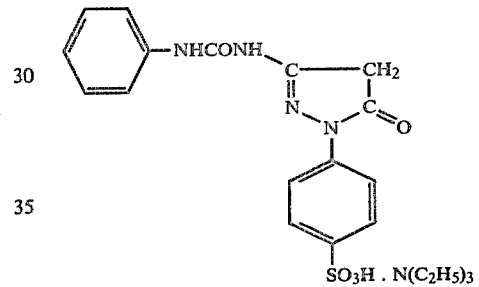
Compound 24
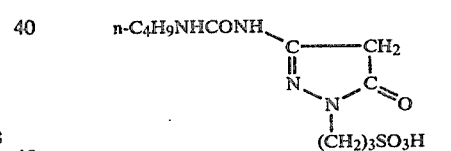
Compound 25
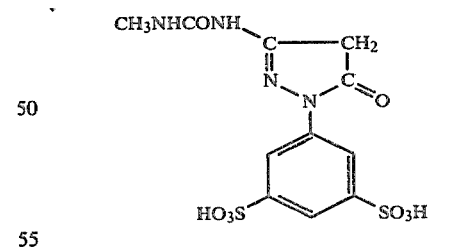
Compound 26
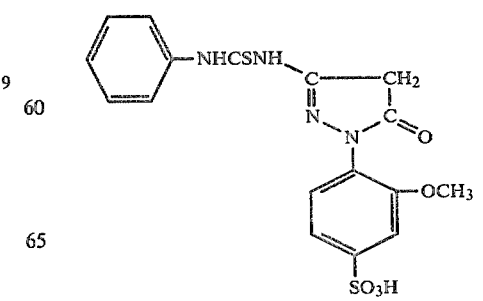

-continued

Compound 27
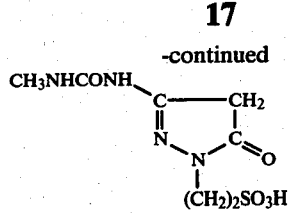

Compound 28
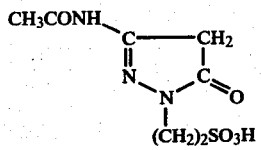

Compound 29
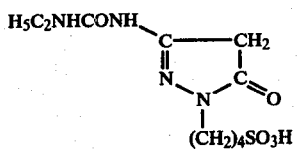

Compound 30
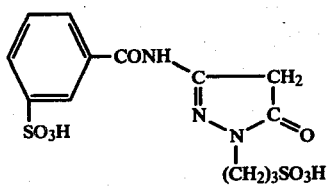

Compound 31
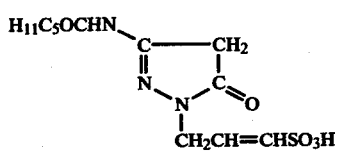

Compound 32
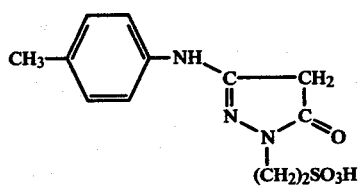

Compound 33
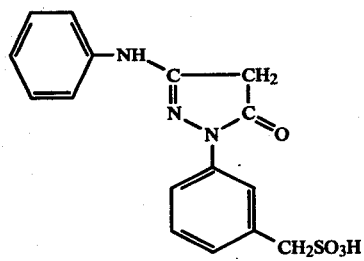

Compound 34
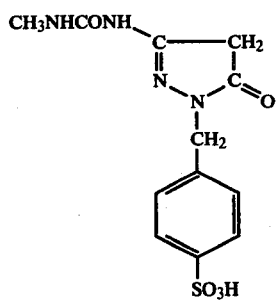

The present invention will be illustrated in more detail by the following non-limiting examples.

EXAMPLE 1

3-Methylureido-1-(p-sulfophenyl)-5-pyrazolone Triethylamine Salt

Into 30 ml of acetonitrile was dissolved 15.9 g of ethyl$\beta$-amino-$\beta$-ethoxy acrylate, and 6 g of methyl isocyanate was added thereto. The resulting mixture was allowed to stand at room temperature for 2 days. Into a mixed solution of 50 ml of methanol, 50 ml of triethylamine and 50 ml of glacial acetic acid there was dissolved 18.8 g of p-sulfophenyl hydrazine, into which was then slowly dropped the above solution in which the esterification reaction had been completed. The solution so obtained was allowed to stand at room temperature for 4 days, whereupon crystals precipitated. These crystals were combined and washed with acetonitrile and then recrystallized from ethanol; thus, 31 g of pale yellow plate-like crystals of the objective compound of a melting point of 248° to 250° C. was obtained.

Elemental Analysis: Calculated for $C_{11}H_{12}N_4O_5S.N(C_2H_5)_3$: C, 49.38:; H, 6.58; N, 16.94. Found: C, 49.35; H, 6.72; N, 16.68.

EXAMPLE 2

3-Methylureido-1-($\gamma$-sulfopropyl)-5-pyrazolone

Into 30 ml of acetonitrile was dissolved 15.9 g of ethyl$\beta$-amino-$\beta$-ethoxy acrylate, and 6 g of methyl isocyanate was added thereto. The resulting mixture was allowed to stand at room temperature for two days. Into a mixed solution of 40 ml of glacial acetic acid and 20 ml of triethylamine there was dispersed 15.4 g of $\gamma$-hydrazinopropane sulfonic acid, and the above ester reaction solution was then added thereto and stirred while heating (95°–100° C.) on a water bath. In a short time, the solution became uniform and it was stirred as it was while heating (95°–100° C.) for 5 hours. The reaction solution was then concentrated under reduced pressure, and 50 ml of ethanol containing 35% by wt hydrogen chloride was then added to the resulting concentrated residue to thereby produce a uniform solution. This solution was allowed to stand in a refrigerator overnight and the crystals which precipitated were collected and recrystallized from methanol; thus, 14.8 g of crystals of the objective compound of a decomposition point of 186° C. was obtained.

Analysis: Calculated for $C_8H_{14}N_4O_5S.H_2O$: C, 32.42; H, 5.44; N, 18.90. Found: C, 32.19; H, 5.24; N, 18.75.

EXAMPLE 3

3-Phenylureido-1-(p-sulfophenyl)-5-pyrazolone Triethylamine Salt

Into 30 ml of acetonitrile was dissolved 4 g of ethyl$\beta$-amino-$\beta$-ethoxy acrylate, and 3 g of phenyl isocyanate was added thereto. The resulting solution was allowed to stand at room temperature for 24 hours. Into a mixed solution of 20 ml of methanol, 6 g of triethylamine and 5 ml of glacial acetic acid there was dissolved 4.7 g of p-sulfophenyl hydrazine, and the above solution, in which the esterification reaction had been completed, was added thereto. The resulting solution was allowed to stand at room temperature for 5 days. The crystals obtained were collected, washed with acetonitrile, and then recrystallized from methanol; thus 7.5 g of crystals of a melting point of 240° to 242° C. was obtained.

Analysis: Calculated for $C_{16}H_{24}N_4O_5S \cdot N(C_2H_5)_3$: C, 55.57; H, 6.15; N, 14.73. Found: C, 55.32; H, 6.11; N, 14.60.

EXAMPLE 4

3-Anilino-1-(p-sulfophenyl)-5-pyrazolone

Into 1.5 l of ethanol were dispersed 118 g of ethyl$\beta$-anilino-$\beta$-ethoxy acrylate and 94 g of p-sulfophenylhydrazine, and 150 g of triethylamine and glacial acetic acid were successively dropped thereinto while heating (95°–100° C.) and stirring. After heating (95°–100° C.) and stirring for 5 hours, the reaction solution was concentrated under reduced pressure. To the residue so concentrated were added 50 ml of water and 120 ml of ethanol containing 35% by wt. hydrogen chloride to provide a uniform solution. This uniform solution was allowed to stand in a refrigerator for one day and one night. The crystals of the objective compound which precipitated had a melting point of 290° to 291° C. and weighed 145 g.

Analysis: Calculated for $C_{15}H_{13}N_3O_4S$: C, 54.38; H, 3.96; N, 12.69. Found: C, 54.21; H, 3.75; N, 12.50.

EXAMPLE 5

3-Acetylamino-1-(p-sulfophenyl)-5-pyrazolone Triamine Salt

To a solution of 15.9 g of ethyl$\beta$-amino-$\beta$-ethoxy acrylate and 11 g of triethylamine in 30 ml of acetonitrile was slowly dropped 7.8 g of acetyl chloride while cooling (10°–15° C.) with water and stirring, and the stirring was continued for 3 hours at 10°–15° C. 18.8 g of p-sulfophenylhydrazine was dissolved in a mixed solution of 50 ml of methanol, 50 ml of triethylamine and 50 ml of glacial acetic acid. To the resulting solution was added the above ester reaction solution at one time, and the system then allowed to stand at room temperature for one week.

This reaction mixture was concentrated under reduced pressure, and the concentrated residue was then dissolved by adding 50 ml of ethanol containing 35% by wt. hydrogen chloride. Upon standing the solution in a refrigerator for one night, crystals precipitated. The crystals were recrystallized from ethanol, whereby 31 g of plate-like crystals of the objective compound of a melting point of 264° to 257° C. was obtained.

Analysis Calculated for $C_{11}H_{11}N_3O_5S \cdot N(C_2H_5)_3$: C, 51.25; H, 6.58; N, 14.04. Found: C, 50.96; H, 6.67; N, 14.02.

EXAMPLE 6

3-Phenylureido-1-($\gamma$-sulfopropyl)-5-pyrazolone

Into a solution of 15.9 g of ethyl$\beta$-amino-$\beta$-ethoxy acrylate in 30 ml of acetonitrile was dropped 12 g of phenylisocyanate while cooling with ice water and stirring, which were reacted for 4 hours while cooling with ice water. The resulting reaction mixture was allowed to stand at room temperature for one night. Into a mixed solution of 50 ml of methanol, 50 ml of triethylamine and 50 ml of glacial acetic acid there was dissolved 18.8 g of p-sulfophenyl hydrazine, to which was slowly added the above ester reaction solution. The mixture so obtained was allowed to stand for 3 hours at room temperature. The reaction mixture was then concentrated under reduced pressure, and 50 ml of ethanol containing 35% by wt. hydrogen chloride was added to the concentrated residue to provide a uniform solution. This uniform solution was allowed to stand in a refrigerator for one day and one night, whereafter the crystals which precipitated were collected and recrystallized from methanol to obtain needle-like crystals of the objective compound having a decomposition point of 220° C. in an amount of 20 g.

Analysis: Calculated for $C_{13}H_{16}N_4O_5S \cdot H_2O$: C, 43.57; H, 5.06; N, 15.64. Found: C, 43.38; H, 5.34; N, 15.67.

EXAMPLE 7

3-n-Butylureido-1-(p-sulfophenyl)-5-pyrazolone Triethylamine Salt

Into 30 ml of acetonitrile were dissolved 15.9 g of ethyl$\beta$-amino-$\beta$-ethoxy acrylate and 10 g of n-butyl isocyanate, and the system then allowed to stand at room temperature for 3 days. Into a mixed solution of 50 ml of methanol, 50 ml of triethylamine and 50 ml of glacial acetic acid was dissolved 18.8 g of p-sulfophenyl hydrazine, to which was slowly added the above ester reaction solution. The resulting solution was allowed to stand at room temperature for 7 days and then concentrated under reduced pressure. The concentrated residue was dissolved by adding 50 ml of ethanol containing 35% by wt. hydrogen chloride thereto. On standing the solution so obtained in a refrigerator for one night, crystals precipitated. The crystals were collected and recrystallized from ethanol, whereupon 26.5 g of needle-like crystals of the objective compound of a melting point of 174° to 176° C. was obtained.

Analysis: Calculated for $C_{14}H_{18}N_4O_5S \cdot N(C_2H_5)_3$: C, 52.73; H, 7.30; N, 15.38. Found: C, 52.57; H, 7.46; N, 15.07.

EXAMPLE 8

3-(N,N-di-n-butyl)amino-1-(p-sulfophenyl)-5-pyrazolone

A mixed solution of 54 g of ethyl$\beta$-(N-di-n-butyl)-amino-$\beta$-ethoxy acrylate, 38 g of p-sulfophenyl hydrazine, 250 ml of ethyl alcohol, 60 g of triethylamine and 36 g of glacial acetic acid was boiled on a steam bath for 8 hours and then concentrated under reduced pressure. To the resulting reddish-brown concentrate there was added 15 ml of concentrated hydrochloric acid (38 wt.%), and the system then allowed to stand in a refrigerator for one night, whereupon crystals precipitated. The crystals were taken out using 100 ml of ethanol and recrystallized from methanol-water (1:1 volume); thus, 60 g of crystals of the objective compound of a melting point of 267° to 269° C. was obtained.

Analysis: Calculated for $C_{17}H_{25}N_3O_4S$: C, 55.57; H, 6.86; N, 11.44. Found: C, 55.28; H, 7.08; N, 11.49.

EXAMPLE 9

3-Morpholino-1-(p-sulfophenyl)-5-pyrazolone Triethylamine Salt

Into 70 ml of ethanol was dissolved 13.5 g of $\beta$-morpholino-$\beta$-ethoxy-acrylic morpholide, and 9.4 g of p-sulfophenyl hydrazine was dissolved in a mixed solution of 30 g of triethylamine and 18 g of glacial acetic acid. The two solutions were then mixed. The resulting mixed solution was boiled on a steam bath for 8 hours. The mixture was then concentrated under reduced pressure to thereby provide a reddish, oily compound, to which 50 ml of isopropyl alcohol and 10 ml of concentrated hydrochloric acid (38 wt%) were added. Upon standing the thus obtained solution in a refrigerator for one night, crystals precipitated. The crystals were collected and recrystallized from ethanol, whereupon 9.8 g of crystals of the objective compound of a melting point of 203° to 205° C. was obtained.

Analysis: Calculated for $C_{19}H_{30}N_4O_5S$: C, 53.51; H, 7.09; N, 13.14. Found: C, 53.42; H, 7.13; N, 13.08.

EXAMPLE 10

3-(3',5'-dimethoxycarbonyl)anilino-1-(3''-sulfopropyl)-5-pyrazolone

Into 2.5 l of methanol were dispersed 105 g of and 46 g of γ-hydrazino-propanesulfonic acid, into which 100 g of triethylamine and then 60 g of glacial acetic acid were dropped while heating on a steam bath (95°–100° C.) and stirring. In a short time, a uniform solution was obtained, and this solution, as it was, was then heated and stirred (95°–100° C. on a steam bath) for 3 hours. The reaction mixture was then concentrated under reduced pressure, and to the concentrated residue was added 120 ml of ethanol containing 35% by wt. hydrogen chloride to provide a uniform solution. This uniform solution was allowed to stand in a refrigerator for one day and one night; thus 96 g of crystals of the objective compound of a melting point of 169° to 170° C. was obtained.

Analysis: Calculated for $C_{16}H_{19}N_3O_8S$: C, 46.49; H, 4.63; N, 10.17. Found: C, 46.21; H, 4.59; N, 10.12.

EXAMPLE 11

3-Benzoylamino-1-(p-sulfophenyl)-5-pyrazolone Triethylamine Salt

Into a mixed solution of 50 ml of methanol, 50 ml of triethylamine and 50 ml of glacial acetic acid there was dissolved 18.8 g of p-sulfophenyl hydrazine, to which 26.3 g of ethylβ-benzoylamino-β-ethoxyacrylate was then added. The resulting solution was allowed to stand at room temperature for one week. The crystals which precipitated were collected and recrystallized from methanol; thus, 32 g of pale yellow crystals of the objective compound of a melting point of 275° to 278° C. was obtained.

Analysis: Calculated for $C_{16}H_{13}N_3O_5S.N(C_2H_5)_3$: C, 57.38; H, 6.13; N, 12.17. Found: C, 57.59; H, 6.25; N, 12.39.

EXAMPLE 12

3-Methanesulfonylamino-1-(p-sulfophenyl)-5-pyrazolone Triethylamine Salt

Into a mixed solution of 50 ml of methanol, 50 ml of triethylamine and 50 ml of glacial acetic acid there was dissolved 18.8 g of p-sulfophenyl hydrazine, to which was added 23.5 g of ethylβ-methanesulfonylamino-β-ethoxyacrylate. The resulting solution was allowed to stand at room temperature for one week. The crystals precipitated were collected and recrystallized from methanol; thus 29 g of plate-like crystals of the objective compound of a melting point of 236° to 238° C. was obtained.

Analysis: Calculated for $C_{10}H_{11}N_3O_6S_2.N(C_2H_5)_3$: C, 44.24; H, 6.03; N, 12.90. Found: C, 44.50; H, 6.25; N, 12.91.

The pyrazolones produced according to the present invention are useful as intermediates for spectral sensitizers or light-absorbing dyes in silver halide photosensitive materials. Cyanine dyes or merocyanine dyes useful as spectral sensitizers can be produced therefrom by a method as described in U.S. Pat. Nos. 3,282,699; 2,526,632, and 3,148,187. Oxonol dyes or hemioxonol dyes useful as light absorbing dyes can be produced be a method as described in British Pat. No. 506,385, U.S. Pat. No. 2,274,282, Japanese Patent Publication No. 22069/1964 and Japanese Patent Laid Open No. 147712/1975 (which corresponds to U.S. Ser. No. 578,798; see specifically pages 22 and 23 of this U.S. Application).

While the invention has been described in detail and with reference to specific embodiments thereof, it will be apparent to one skilled in the art that various changes and modifications can be made therein without departing from the spirit and scope thereof.

What is claimed is:

1. A process for producing 3-substituted amino-5-pyrazolones containing at least one sulfo group represented by formula (I) which comprises reacting a β-substituted amino-β-alkoxy acrylic acid derivative represented by formula (II) and a hydrazine containing at least one sulfo group represented by formula (III) in a mixture of acetic acid and triethylamine,

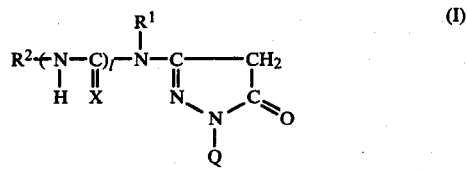

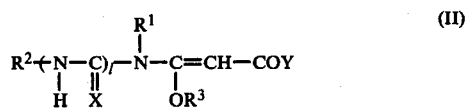

wherein $R^1$ is a hydrogen atom, a perfluoroalkyl group containing 1 to 12 carbon atoms, an alkyl group containing 1 to 18 carbon atoms, a cycloalkyl group containing 5 to 7 carbon atoms, an aralkyl group containing 7 to 13 carbon atoms or a monocyclic aryl group;

$R^2$ is a perfluoroalkyl group containg 1 to 12 carbon atoms, an alkyl group containing 1 to 18 carbon atoms, an alkenyl group containing 2 to 5 carbon atoms, a cycloalkyl group containing 5 to 7 carbon atoms, an aralkyl group containing 7 to 13 carbon atoms, a monocyclic or bicyclic aryl group or a carboxylic acyl group containing 2 to 8 carbon atoms, an alkylsulfonyl group containing 1 to 4 carbon atoms or an aryl sulfonyl group; l is 0 or 1 and where l is 0, $R^1$ and $R^2$ may combine with each other to form a pyrrolidine, piperidine, morpholine or piperazine ring;

$R^3$ is an aliphatic group containing 1 to 6 carbon atoms or an aralkyl group containing 7 to 8 carbon atoms;

X is oxygen or sulfur;

Y is a hydroxy group, an alkoxy, an aralkoxy group or a primary, secondary or tertiary amino group; and Q is an alkyl group containing 1 to 6 carbon atoms and at least one sulfo group, a substituted alkyl group containing 2 to 5 carbon atoms and one substituent thereof is a sulfo group and another substituent is a hydroxy group, an alkoxy group, a halogen atom or an alkenyl group, whose total carbon atom number exclusive of those in the substituents is not more than 5, an aryl group containing at least one sulfo group, or an aralkyl group containing at least one sulfo group.

2. The process according to claim 1 wherein the molar ratio of the compound of formula (II) to the compound of formula (III) is 5:1.

3. The process according to claim 1 wherein the molar ratio of the compound of formula (II) to the compound of formula (III) is 3:1.

4. The process according to claim 1 wherein the molar ratio of the compound of formula (II) to the compound of formula (III) is 1.5:1.

5. The process according to claim 1, wherein the sulfo group is in the form of a free acid or an organic base salt.

6. The process according to claim 1, wherein the molar ratio of the triethylamine to the sulfo group-containing hydrazine represented by formula (II) is about 0.5 to about 50 and the molar ratio of the acetic acid to the triethylamine is about 0.1 to about 20.

7. The process according to claim 1, wherein the molar ratio of the triethylamine to the hydrazines is about 0.5 to about 20 and the molar ratio of the acetic acid to the triethylamine is about 0.5 to about 10.

8. The process according to claim 6, wherein the molar ratio of the triethylamine to the hydrazines is about 0.5 to about 10 and the molar ratio of the acetic acid to the triethylamine is about 0.5 to about 5.

9. The process according to claim 3, wherein the reaction is effected at temperatures of from about 0° C. to the boiling point of a mixture of an acetic acid-triethylamine or acetic acid-triethylamine-organic solvent.

10. The process according to claim 1, wherein said acid derivative represented by the formula (II) is ethyl-β-methylureido-β-ethoxyacrylate, the hydrazine represented by the formula (III) is p-sulfo phenylhydrazine.

11. A process for producing 3-substituted amino-5-pyrazolones according to claim 3 wherein the β-substituted amino-β-alkoxy acrylic acid derivative represented by formula (II) is synthesized by the reaction of a β-amino-β-alkoxyacrylic acid ester with an acid halide, sulfonyl chloride, isocyanate or thioisocyanate.

12. The process according to claim 1, wherein said pyrazolone of formula (I) is selected from the group consisting of

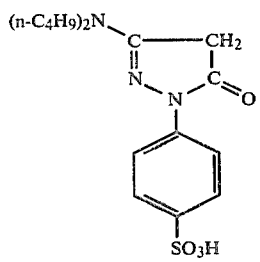

-continued

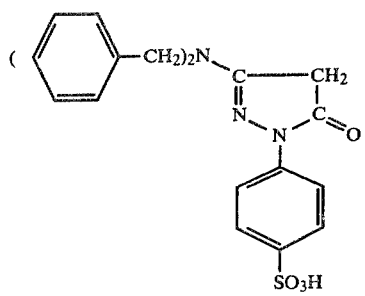

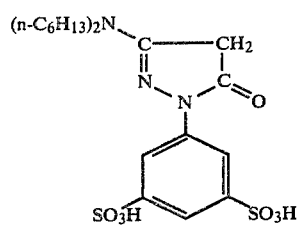

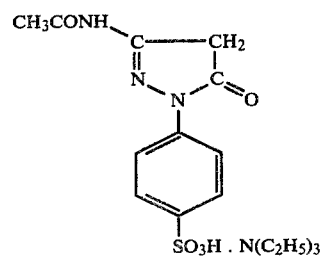

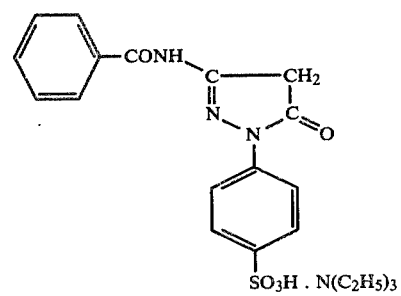

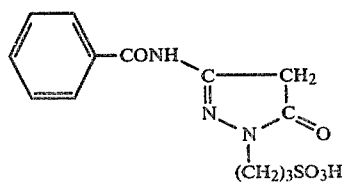

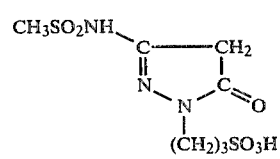

-continued
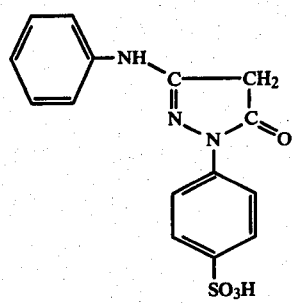
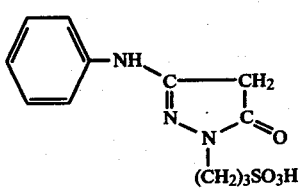
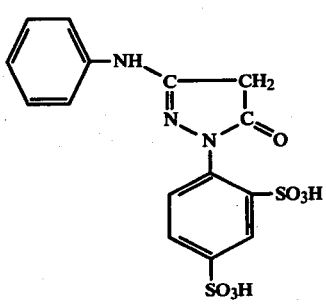
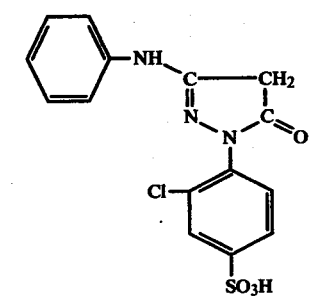
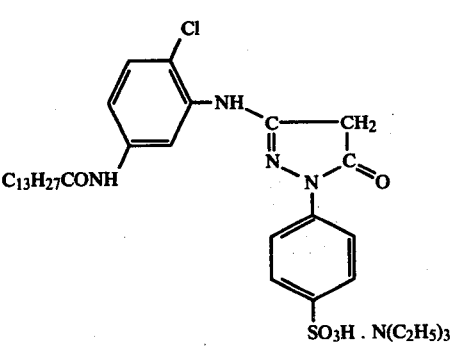
-continued
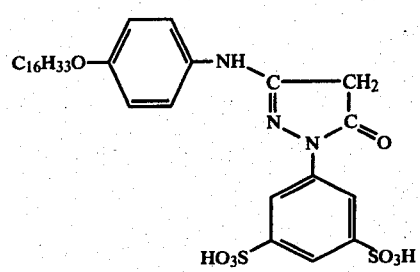
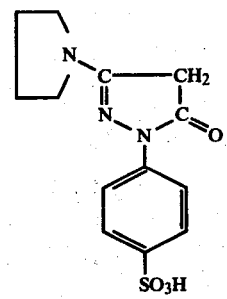
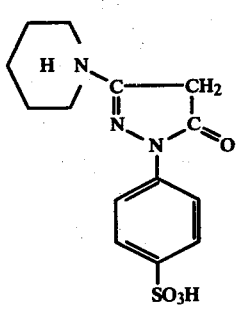
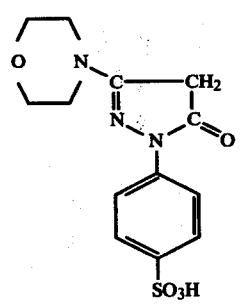
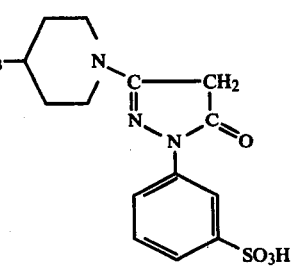

-continued
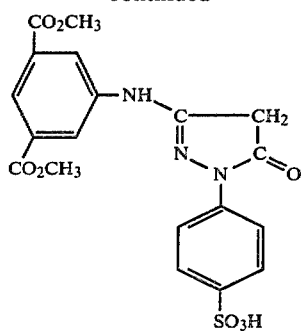
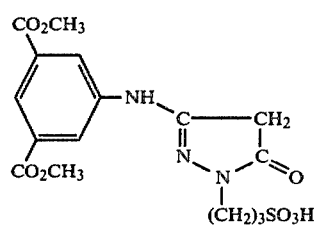
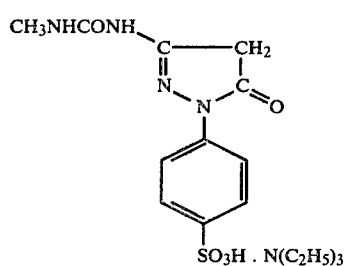
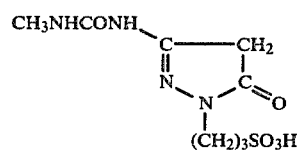
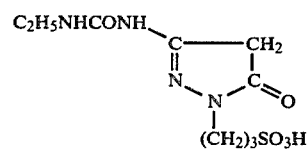
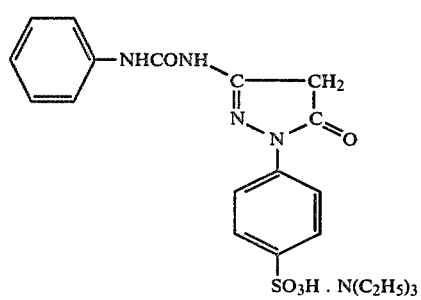
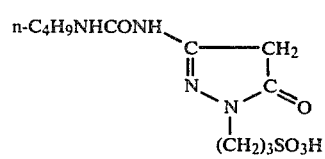
-continued
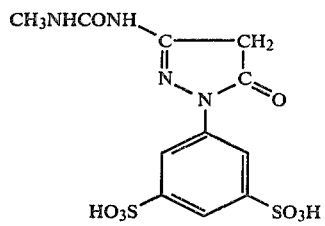
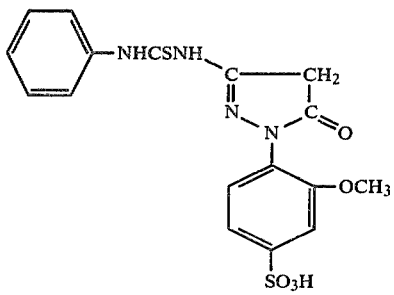
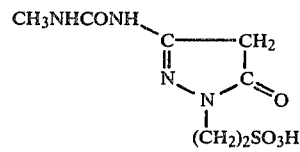
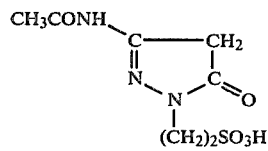
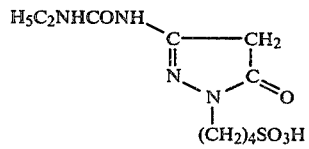
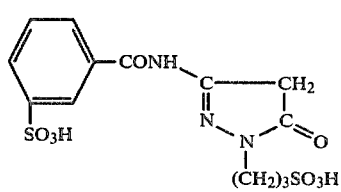
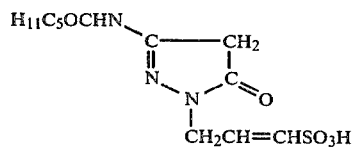
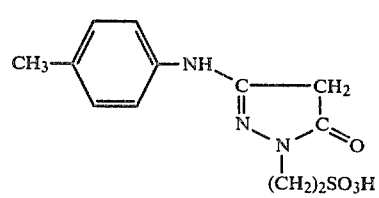

-continued
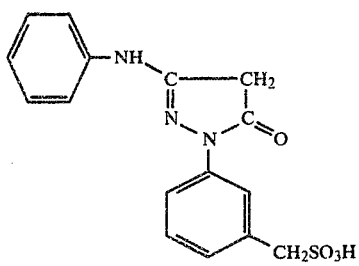
-continued
or
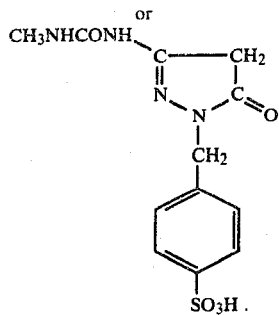
* * * * *